United States Patent
Padilla et al.

[11] Patent Number: 6,059,758
[45] Date of Patent: May 9, 2000

[54] PROPHYLACTIC SHEATH FOR PROTECTING AND STORING DIFFERENT TYPES OF MEDICAL NEEDLES

[75] Inventors: William Padilla, Sandy; Garlyn W. Hendry, Salt Lake City, both of Utah

[73] Assignee: Merit Medical Systems, Inc., South Jordan, Utah

[21] Appl. No.: 08/950,634

[22] Filed: Oct. 15, 1997

[51] Int. Cl.[7] .................................................. A61M 5/00
[52] U.S. Cl. ............................................ 604/263; 604/192
[58] Field of Search .................................. 604/192, 263, 604/187, 197, 198, 162, 171

[56] References Cited

U.S. PATENT DOCUMENTS

| | | | |
|---|---|---|---|
| 4,139,010 | 2/1979 | Dykastra .............................. | 128/221 |
| 4,610,667 | 9/1986 | Pedicano et al. ..................... | 604/192 |
| 4,629,453 | 12/1986 | Cooper ................................ | 604/192 |
| 4,654,034 | 3/1987 | Masters et al. ...................... | 604/192 |
| 4,659,330 | 4/1987 | Nelson et al. ....................... | 604/192 |
| 4,735,617 | 4/1988 | Nelson et al. ....................... | 604/192 |
| 4,740,204 | 4/1988 | Masters et al. ...................... | 604/192 |
| 4,799,927 | 1/1989 | Dods et al. .......................... | 604/172 |
| 4,826,488 | 5/1989 | Nelson et al. ....................... | 604/192 |
| 4,883,470 | 11/1989 | Haindl ................................. | 604/192 |
| 5,000,742 | 3/1991 | Morrison ............................. | 604/192 |
| 5,002,536 | 3/1991 | Thompson et al. .................. | 604/192 |
| 5,021,049 | 6/1991 | Howard .............................. | 604/192 |
| 5,116,325 | 5/1992 | Paterson ............................. | 604/192 |
| 5,163,915 | 11/1992 | Holleron ............................ | 604/192 |
| 5,242,421 | 9/1993 | Chan .................................. | 604/198 |
| 5,279,578 | 1/1994 | Cooke ................................ | 604/192 |
| 5,334,173 | 8/1994 | Armstrong, Jr. .................... | 604/263 |
| 5,451,213 | 9/1995 | Teicher et al. ..................... | 604/192 |
| 5,720,727 | 2/1998 | Alexander et al. ................. | 604/110 |

*Primary Examiner*—Corrine McDermott
*Assistant Examiner*—Cris Rodriguez
*Attorney, Agent, or Firm*—Workman, Nydegger, Seeley

[57] ABSTRACT

Prophylactic needle guards or sheaths for protecting medical needles and persons using the medical needless either before or after use of the needle. The prophylactic needle guards have a flared portion in order to provide safe insertion of a medical needle into a protective hollow body portion. The needle guard includes structures which are configured to engage at least one of a variety of differently sized and configured wing portions found in medical needles. The needle guard may include a pair of projections that engage corresponding holes within the wing portions of medical needles that includes wings too large to enter the flared portion. Alternatively or in addition to the projections, the needle guard may include one or more interior annular grooves disposed on an inner surface of the flared portion that engage the wing portions of medical needles that have wings that are small enough to enter the flared portion.

19 Claims, 4 Drawing Sheets

PROPHYLACTIC SHEATH FOR PROTECTING AND STORING DIFFERENT TYPES OF MEDICAL NEEDLES

BACKGROUND OF THE INVENTION

1. The Field of the Invention

The present invention is in the field of prophylactic sheaths for protecting or shielding medical needles. Particularly, the present invention relates to prophylactic sheaths for protecting or shielding medical needles during handling, storage, use, reuse and disposal of medical needles.

2. Relevant Technology

Needles, such as those used in the medical arts, are typically equipped with a removable prophylactic sheath to protect the needle from damage, to keep the needle sterile during storage and to prevent accidental puncture of the user. Although traditional prophylactic sheaths may adequately protect the needle from damage, keep the needle sterile and prevent accidental puncture before use, there has been a problem with accidental needle punctures after use, especially during reinsertion of the needle into the prophylactic sheath.

While it may hurt to miss the prophylactic sheath and puncture one's self with a sterile needle, it typically has no long lasting consequences. It can, however, be a different story if the handler has previously used the medical needle to inject or extract fluids from a patient. For example, a medical provider is often not aware whether a patient is carrying a communicable disease. With the increasing prevalence of communicable diseases, such as hepatitis and AIDS, medical providers must assume that every patient has a communicable disease. Hence, an accidental needle puncture with a medical needle that has been used to extract fluid from, or inject fluid into, a patient is a serious concern that could even be a matter of life or death.

Figure 1A:
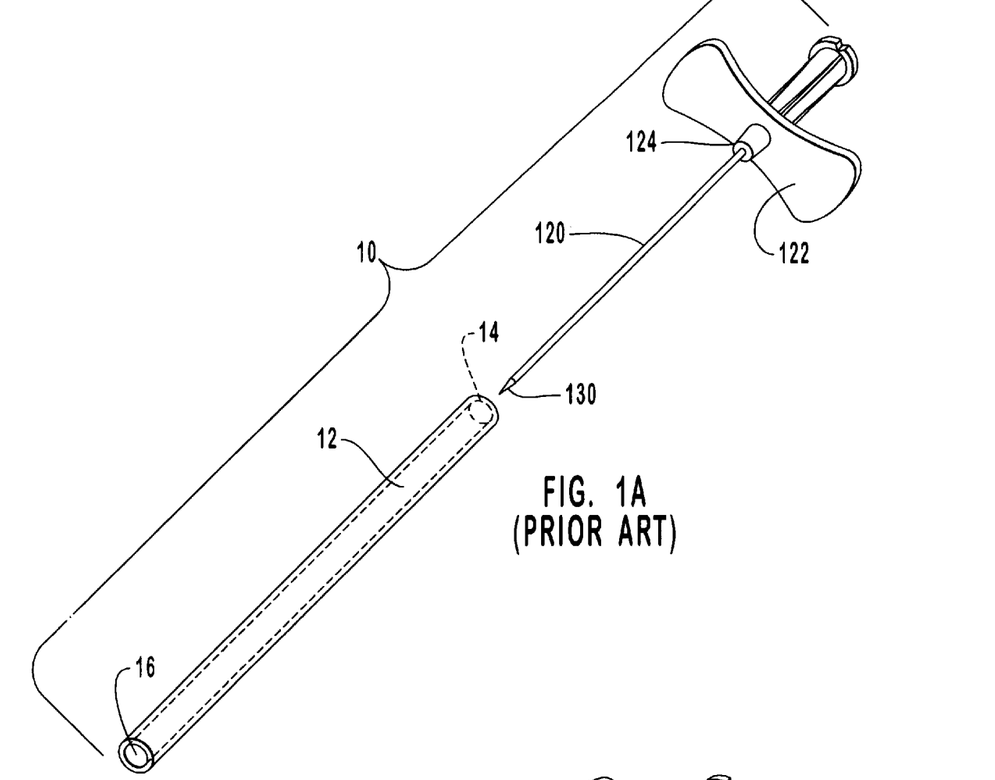
FIG. 1A is a perspective view of a prior art prophylactic sheath and a medical needle having a wing portion being inserted into the prophylactic sheath.
Figure 1B:
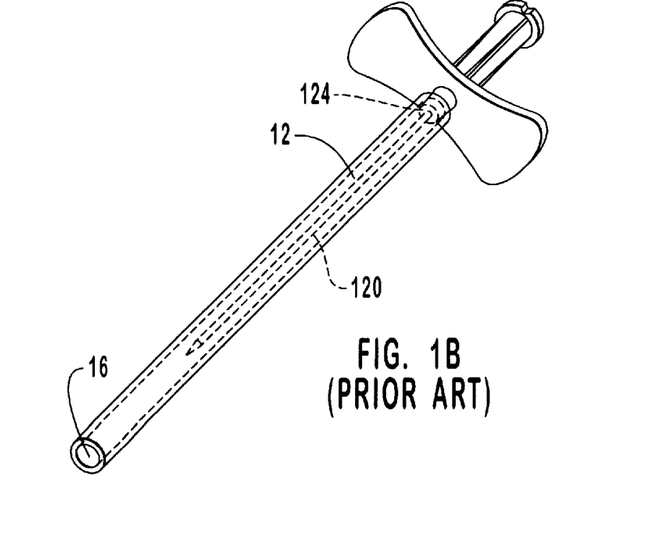
FIG. 1B is a perspective view of a prior art prophylactic sheath and a medical needle having a wing portion engaged in the prophylactic sheath.

Traditional sheaths used to package medical needles prior to use, as illustrated in FIG. 1A and 1B, typically comprise a thin tube 12 manufactured from flexible plastic having relatively small openings at both of ends 14 and 16. Any type of medical needle can be inserted into either end of the packaging sheath 12, including winged needles 120 having wing portions 122 as depicted in FIGS. 1A and 1B. The sheath 12 fits around a hub portion 124 of the needle 120 as a sleeve and engages the medical needle in a press-fit type engagement. The sheath 12 is sized to fit the size of the hub portion 124 and can vary accordingly.

When the medical needle 120 is reinserted back into the packaging sheath 12 after being used, a handler commonly holds the medical needle in one hand and the prophylactic sheath in the other hand. If then, for some reason, such as lack of attention, dim lighting, or an unsteady hand, the handler misgauges the entry of the tip 130 of needle into the opening in sheath 12, the tip 130 of the needle can easily puncture the handler's fingers, hands or other parts of the handler's body. Because of the small target provided by openings 14 and 16, the risk of accidental punctures with contaminated needles is high.

In partial response to the problem of accidental needle punctures, prophylactic sheaths have been provided that include an enlarged conical opening, which provide a larger entry into the prophylactic sheath (not shown). Such sheaths have extending form the conical opening a hollow cylindrical portion similar in design to the sheaths shown in FIGS. 1A and 1B. Such sheaths typically engage the bottom portion of the hub of the medical needle in a press-fit engagement within the end of the hollow cylindrical portion proximal to the conical portion. Although the inclusion of an enlarged opening within prophylactic sheaths may decrease the occurrence of accidental needle punctures, such sheaths have other drawbacks.

One problem is that it is difficult to determine when a needle is securely engaged within the neck region of a prophylactic sheath having an enlarged opening. There is no real indicator that the medical needle has been securely engaged in the prophylactic sheath and, because engagement occurs between the hub and an interior portion of the sheath, it may often be difficult to visually determine if engagement has occurred. Unfortunately, if the needle is not securely engaged within the prophylactic sheath, the needle could fall out of the prophylactic sheath and cause damage or harm to one handling the needle. Moreover, if the diameter of the hub portion 124 differs from needle to needle, a practitioner would have to find a sheath that provided the correct fit, further increasing the risk of improper engagement and risk to the user.

Additionally, typical prophylactic sheaths having an enlarged opening are only adequate in engaging medical needles in a press-fit engagement which have wing portions sized to fit within the conical opening such that the hub portion 124 of the needle may be press fit into the hollow cylindrical portion. As such, medical needles having wing portions which extend so wide that they cannot fit within the conical opening will likely be incapable of forming a press-fit engagement within the cylindrical portion of the sheath. This is because the wings may obstruct entry of the medical needle into the enlarged opening, such that engagement between the hub portion of the needle and the cylindrical portion of the prophylactic sheath is prevented. In other words, the wing portion of the medical needle contacts the outer edge of the enlarged opening, which prevents the hub from reaching the intended point of engagement. This being the case, there are presently no adequate prophylactic sheaths having enlarged openings that can accommodate medical needles having wider wing portions.

In view of the foregoing, it is apparent that there remains a need for a prophylactic sheath having an enlarged opening that is capable of accepting and securely engaging medical needles having a variety of differently-sized wing portions.

In particular, there is a need for a prophylactic sheath having a enlarged opening that is capable of universally accepting medical needles having both narrow-wing portions as well as wide-wing portions in a manner which securely engages either type of needle.

In addition, it would be an advancement in the art to provide a prophylactic sheath which could accommodate and securely engage medical needles having varying-sized hub portions without having to provide a separate sheath for each hub portion size.

It would be a further improvement in the art to provide prophylactic sheaths which provide a definite indicator to the user that the needle inserted therein has been reliably and securely engaged by the sheath.

Such prophylactic sheaths for reliably and securely protecting a variety of differently sized medical needles are disclosed and claimed herein.

SUMMARY AND OBJECTS OF THE INVENTION

It is, therefore, an object of the present invention to provide a prophylactic needle guard or sheath having an enlarged or flared portion for facilitating the insertion of medical needles therein.

It is another object of the present invention to provide a prophylactic needle guard or sheath having a flared portion that is capable of accepting and securely engaging medical needles having a variety of differently-sized wing portions.

It is an additional object of the present invention to provide a prophylactic needle guard or sheath that is capable of accepting and securely engaging medical needles having a variety of differently-sized hub portions.

It is a further object of the present invention to provide a prophylactic needle guard or sheath which includes means for allowing a user to be certain that the medical needle has been reliably and securely engaged by and within the prophylactic sheath.

To achieve the foregoing objects, and in accordance with the present invention as embodied and broadly described herein, the present invention is directed to a needle guard or sheath having a flared portion to provide safe insertion of the needle into a protective hollow body portion. The needle guard accepts and securely engages a variety of different types of medical needles to guard against accidental needle puncture and breakage. In particular, the inventive needle guard has the ability to accept and engage medical needles having a variety of differently-sized wing and hub portions, including wings that will fit within the flared portion and those that are too wide to fit within the flared portion.

In accordance with the present invention, it has been discovered that a needle guard having a flared portion can be adapted to accept a medical needle having varyingly-sized wing portions by designing the flared portion to have means for engaging needles having wider wings and needles having narrower wings. Hence, medical needles having wing portions of widely varying sizes can be safely inserted, engaged, stored and properly disposed thereby.

As used herein, the term "wider wing" refers to wing portions of a medical needle that are too wide to fit within the flared portion of a needle guard. Conversely, the term "narrower wing" portion refers to wing portions of a medical needle that are capable of fitting into the flared portion of a particular needle guard. Whether the wing portion is of the "wider wing" or "narrower wing" variety is a function of both the size of the wing portion extending from the medical needle and also the size of the flared portion. Thus, the wider the flared portion the more types of needles that will fall within the category of having narrower wing portions since wings of greater size will tend to fit within the larger flared portion. Conversely, the narrower or smaller the flared portion, the fewer the types of needles that will fall within the category of having wider wing portions since the flared portion will exclude more sizes of wing portions.

The means for engaging the medical needle differ for narrower winged needles compared to wider winged needles. Typically, a projection extending form an outer edge or lip of the flared portion of the needle guard will provide means for engaging a medical needle having a wider wing portion. In particular, the projection will engage a corresponding opening in the wing portion of the medical needle in a press-fit type engagement. Typically, the flared portion will include a pair of projections that engage corresponding holes in either of the wing portions to restrict movement of the needle once engaged by the projections.

In contrast, narrower winged needles will be engaged by means of a corresponding annular groove on the inner surface of the flared portion. The annular groove will be located such that it will have a diameter substantially similar to the transverse width of the wing portions of the narrower winged needle. Typically, the wings will engage the annular groove in a snap-fit type of engagement. When inserted, the wings will be deflected slightly by the camming action of the angled flared portion until engagement with the annular groove is achieved, whereupon the wings, being of an elastic nature, will snap back and re-extend into their original orientation within the groove. The groove will tend to retain the wings, and therefore the needle, in place unless a withdrawing force great enough to cause deflection of the wings in applied. Although the annular groove will only be able to engage wings of a particular width, or within a narrow range of sizes, the flared portion can include a plurality of annular grooves located and sized to engage variously sized wings of the narrower wing variety. Obviously, the larger the flared portions, the greater the number of differently sized annular grooves that can be provided.

Either the projection used to engage wings of the wider wing variety or the annular groove used to engage wings of the narrower wing variety provide indication means for indicating to the user that a respective needle has been reliably and securely engaged by the sheath. In the case of a wider-winged needle, the user can see when the projections and the holes have been reliably engaged in the aforementioned press-fit engagement. In the case of using a plurality of projections, rotation of the needle is prevented upon engaging the needle within the protective sheath. On the other hand, in the case of a narrow-winged needle, the user will feel and/or hear when the wings have been snapped into place within the annular groove.

In either case, the means for engaging the wings of the medical needle should be such that the sheath/needle combination can be inverted without the needle falling out of the sheath. In addition, the tightness of the fit between the engagement means and the wings can be varied as desired to provide varying levels or strengths of engagement.

In a preferred embodiment of the present invention, the needle guard will comprise an elongated hollow body for accepting the needle portion of a medical needle; a hollow flared portion extending radially and axially from an end of the hollow body for facilitating entry of a needle into the elongated hollow body, the flared portion having a first end comprising a lip defining an opening, and a second end defining a more narrow opening connected and leading to the hollow body; at least one projection extending from the lip for engaging a corresponding opening and recess within the wing portion of a wider winged medical needle when the medical needle is inserted within the needle guard; and at least one interior annular groove on the inner surface of the flared portion disposed between the first end and the second end of the flared portion for receiving the wing portion of a narrowerwinged medical needle.

These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

The present invention is directed to prophylactic needle guards or sheaths having a flared portion to increase the ease and accuracy of inserting a needle therein. The inventive needle guards are capable of accepting and securely engaging medical needles having a variety of differently-sized wing and hub portions. To this end, the prophylactic sheaths provide means for engaging the wing portion of winged medical needles. In addition, the present invention is directed to needle guards that include means for indicating when the medical needle inserted therein has been securely and reliably engaged within the needle guard.

As used herein, the terms "needle guard" is defined as a prophylactic sheath, tubing or other protective apparatus for accepting and securely engaging medical needles having wing portions.

As used herein, the term "medical needle" refers to any type of needle used in the medical field, including, but not limited to syringes, hypodermic needles, angiographic needles and obturator needles. Furthermore, as used herein the term "medical needle" refers to medical needles having any type of wing portion known in the art.

As used herein, the term "wing portion" refers to a laterally extending portion or flap that projects in a generally orthogonal direction from the end of the medical needle and which is used for connecting the needle to another device or simply handling the needle.

Accidental needle punctures by handlers of medical needles have long been a problem in the medical field. They can occur at any time during the useful life of the needle, although they are far more dangerous after the needle has been used and exposed to a patient's blood. Simply reinserting the needle into the sheath in which the needle was originally packaged would offer adequate protection in most cases if not for the fact that reinsertion is often problematic due to the relatively small opening of the packaging sheaths. With the increasing prevalence of communicable diseases, such as hepatitis and AIDS, accidental needle punctures can result in serious illness or even death. Hence, the risks associated with accidental needle punctures have, in recent years, become greatly magnified.

In partial response to the problem of accidental needle punctures, prophylactic sheaths have been developed which include an enlarged opening to provide a larger entry into the prophylactic sheath and to guide the needle into the narrower sheath portion. Like sheaths used in packaging medical needles, conventional sheaths having an enlarged opening engage the hub portion of the needle below the wings in a press-fit manner. While a press-fit engagement is capable of providing a secure engagement in some cases, slight differences in the diameter of the hub portion of the needle can either compromise the integrity of the engagement if significantly smaller or larger than the diameter of the neck of the sheath.

Moreover, such sheaths are incapable of engaging needles having wings that are wider than the width of the enlarged opening. The wings effectively prevent insertion of the needle far enough to allow the hub to be received in a press-fit engagement within the neck of the sheath. An ineffective engagement between needle and sheath presents the real danger of the needle falling out of the sheath if inverted or disturbed. As set forth above, the prophylactic sheaths of the present invention address and overcome these problems.

Figures 2A, 2B:
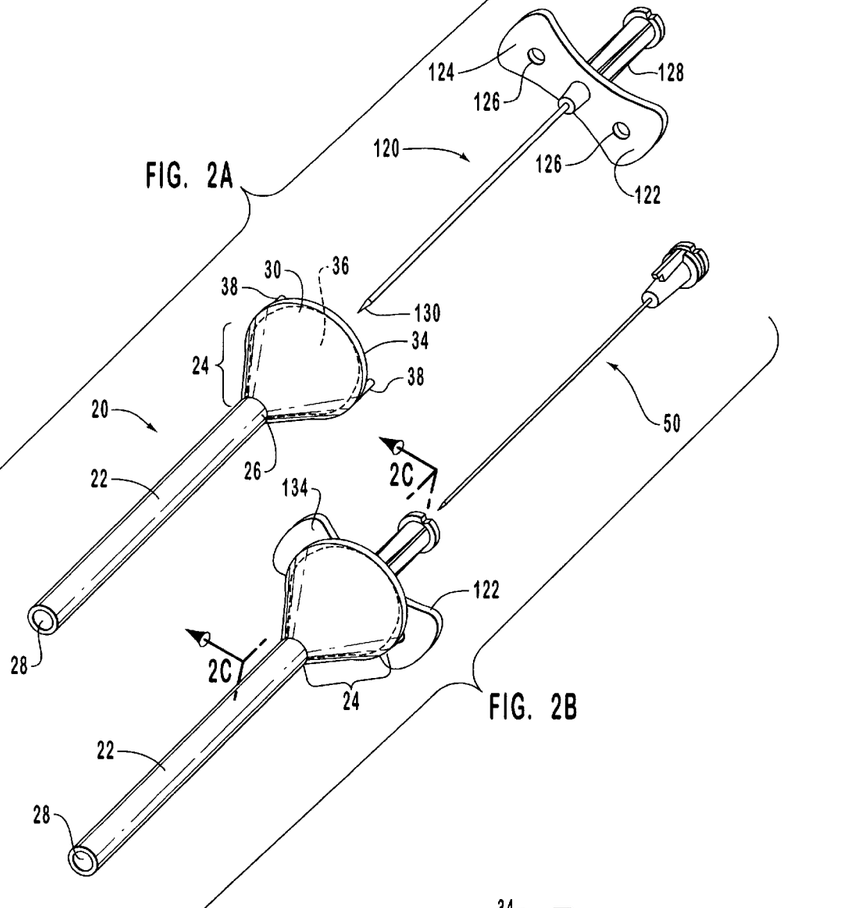
FIG. 2A is a perspective view of a needle guard of the present invention showing a medical needle having a wider-wing portion being inserted into the needle guard.
FIG. 2B is a perspective view of a needle guard of the present invention showing a medical needle having a wider-wing portion, where the needle is securely engaged with the needle guard.
Figure 2C:
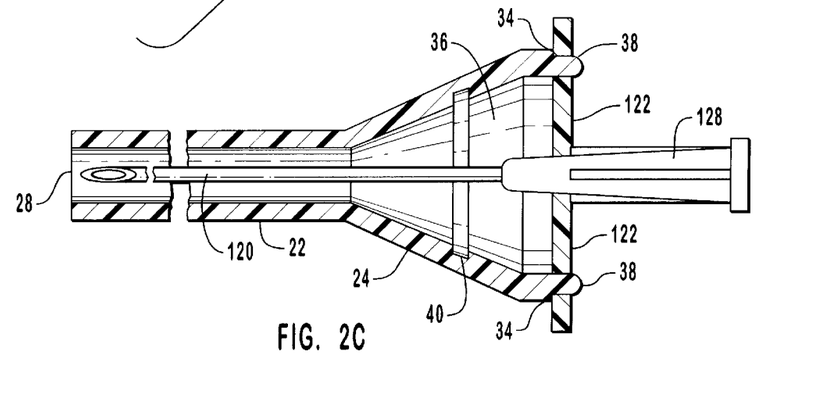
FIG. 2C is a side cross-sectional view of the flared portion of a needle guard of the present invention cut along line 2C—2C of FIG. 2B.
Figures 3A, 3B:
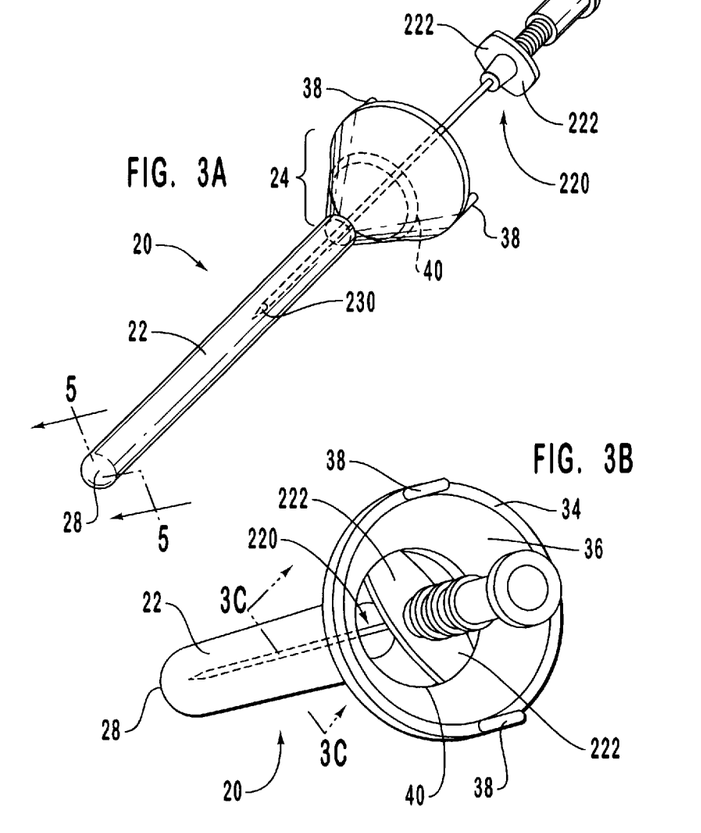
FIG. 3A is a perspective view of a needle guard in accordance with the present invention showing a medical needle having a narrower-wing portion being inserted into the needle guard.
FIG. 3B is a perspective view of a needle guard in accordance with the present invention showing a medical needle having a narrower-wing portion securely engaged in the needle guard.
Figure 3C:
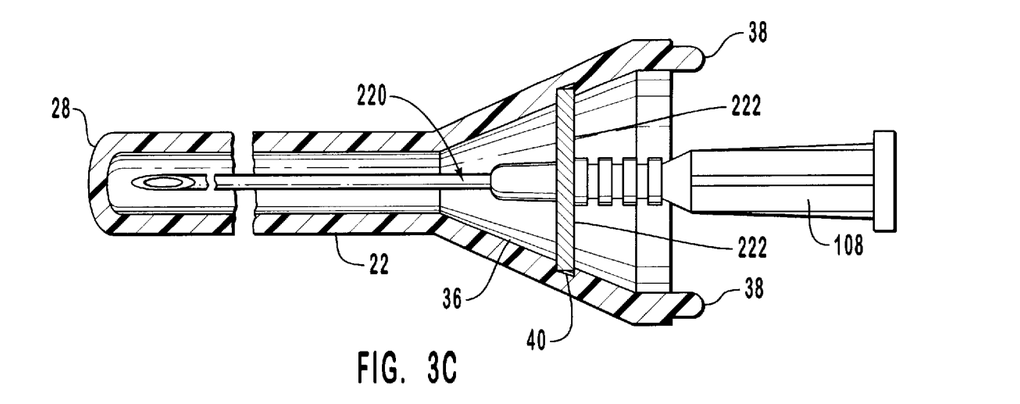
FIG. 3C is a side cross-sectional view of the flared portion of a needle guard in accordance with the present invention cut along line 3C—3C of FIG. 3B.
Figures 4, 5A:
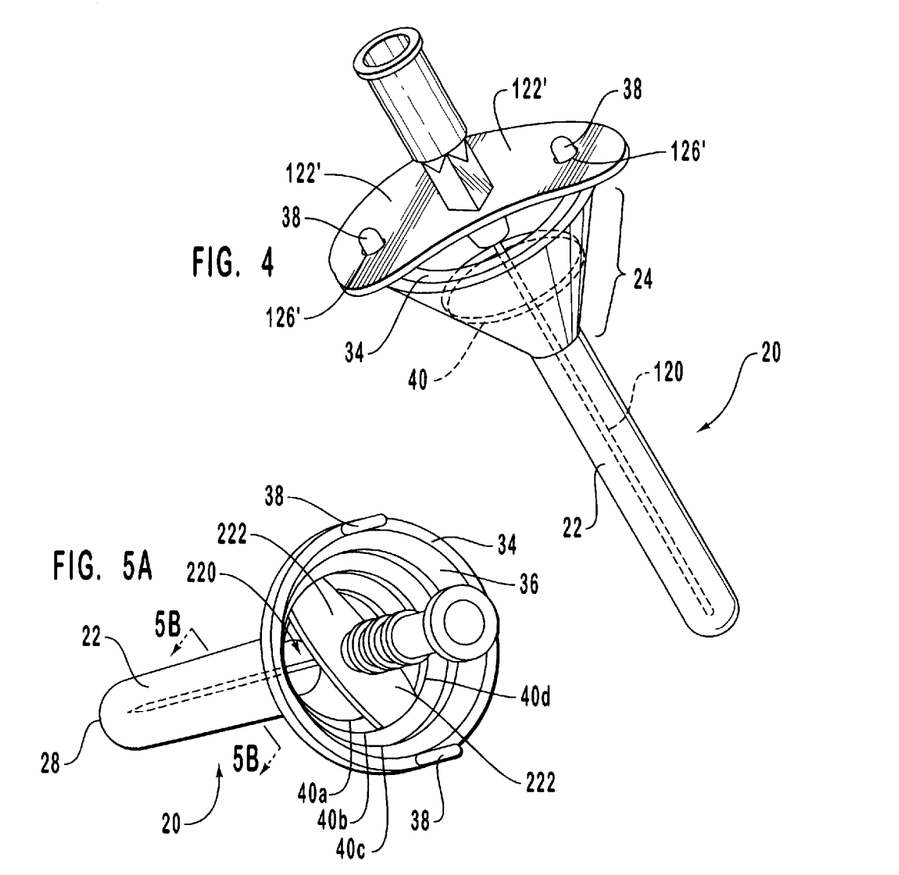
FIG. 4 is a perspective view of a medical needle having an alternative wider-wing portion in secure engagement with the needle guard of the present invention.
FIG. 5A is a perspective view of a prophylactic sheath of the present invention having a plurality of interior annular grooves.

Referring now to FIGS. 2–4, a needle guard 20 according to the present is depicted, which includes an elongated hollow body 22, which is preferably generally cylindrical, and a hollow flared portion 24 extending radially and axially from a first end 26 of the hollow body 22. The hollow body 22 also includes a second end 28 distal to the hollow flared portion 24.

The flared portion 24 includes a first end 30 distal to the hollow body 22 and a second end 32 proximal to, and integrally connected with, the proximal end 26 of the hollow body 22. The flared portion 24 further includes an outer lip 34 and a hollow interior 36. The flared portion 24 facilitates insertion of a needle 120 by greatly increasing the effective opening of the sheath. The inwardly sloping hollow interior 36 of the flared portion 24 guides the tip 130 of the needle into the hollow body 22, which provides a prophylactic cover or sheath in order to protect the needle and the user.

Besides providing greater ease and security in inserting a medical needle within the elongated hollow body 22, the needle guard 20 of the present invention also provides means for engaging a medical needle inserted therein in order to ensure that the needle remains within the protective sheath when desired such that the needle will not inadvertently fall out of the sheath. Although prior art sheaths typically engage the hub portion 124 of the medical needle when in a press-fit engagement, the needle guard 20 of the present invention provides means for engaging the wing portions of the medical needle in order to provide a more secure engagement. Depending on the breadth of the wing portions 122, the needle guard 20 will include appropriate structure corresponding to the type of wing structure in question, whether of the wider or narrower variety. In the case of a wider wing structure that cannot fit within the flared portion 24, the means for engaging the wing portions will be disposed on the lip 34 of the needle guard 20. In the case of a narrower wing structure that can fit within the flared portion 24 of the needle guard 20, the means for engaging the wing portion of the needle will be located within the interior of the flared portion 24.

As depicted in FIGS. 2A–2C, the means for engaging a wider-winged medical needle 120 comprises a pair of projections 38 which engage corresponding openings or recesses 126 within wings 122 of the medical needle 120. As the medical needle 120 is inserted within needle guard 20, it is oriented by the user in a manner such that the projections 38 engage recesses 126 of the medical needle 120 in a press-fit engagement. Although it would certainly be within the scope of the present invention to provide a single projection 38 that could reliably engage either of holes 126, it is preferable to include both projections 38 in order to restrict movement of the medical needle once engaged within needle guard 20.

Alternatively the means for engaging the medical needle 120 might include other structures in addition to or instead of projections 38 so long as they can provide a secure engagement with the wing portions 122 of the medical needle 120 in order to prevent inadvertent separation of the needle 120 from the needle guard 20. For example, the needle guard 20 can alternatively include one or more flexible prongs that are configured to engage the holes or recesses 126 of the medical needle 120 in a snap-fit rather than a press-fit engagement (not shown). By "snap-fit" it is meant that the prongs (not shown) flex and then reextend during engagement such that the user feels or hears a snap, indicating that engagement has occurred. Nevertheless, projections 38 are preferred since they are easily and simply molded into the needle guard 20 and because the holes 126 are easily formed within the wings 122 of medical needle 120.

As further illustrated in FIG. 2B, an obturator 50 can be inserted into and reside within the medical needle 120. Typically, the obturator 50 includes mechanical features which engage an outer sleeve 128 of the medical needle 120 such that the obturator will not inadvertently separate from the medical needle 120. In this fashion, the needle guard 20 can simultaneously protect the combination of the obturator 50 and the medical needle 120. However, it should be pointed out that an obturator 50 could also be used in conjunction with a medical needle having narrower wings (not shown), such as those depicted hereinafter in FIGS. 3A–3C.

Whether or not an obturator 50 is used in conjunction with a medical needle 120, the user will know when the needle 120 has been securely and reliably engaged within needle guard 120 by observing that the projections 38 have been inserted through the holes 126. In addition, secure engagement utilizing two holes will generally restrict movement of the medical needle 120.

In the case where the medical needle includes wings of the narrower variety such that the wings can fit within the flared portion 24, the means for engaging the medical needle will alternatively be disposed within the flared portion 24. As depicted in FIGS. 3A–3C, the means for engaging a narrower winged needle 220 comprises an interior annular groove 40 disposed within the interior of the flared portion 24. Annular groove 40 is preferably situated such that it will have a diameter that corresponds to the width of the narrower wings 222 of an alternative medical needle 220. As with any needle, the tip 230 is guided toward the hollow sheath 22 by means of the flared portion 24.

Due to the angled nature of the flared portion 24, the diameter of the interior annular groove 40 will vary depending upon where it is located within the flared portion 24. In order to accommodate winged portions 222 that tend to be narrower in width, the interior annular groove will tend to have a smaller diameter and be situated where the flared portion 24 is narrower. Conversely, in order to accommodate wings 222 that tend to be wider in width, but yet which still fit within the hollow interior 36 of flared portion 24, the interior annular groove 40 will tend to have a larger diameter and be situated where the flared portion 24 is wider. The width and depth of the groove can vary depending on the quality of fit desired.

The location and diameter of the interior annular groove 40 will be such that the wings 222 will be deflected somewhat when the needle 220 is inserted within the needle guard 20 such that they will initially flex until engagement with the annular groove 40 is achieved. Thereupon, the wings 222, owing to their somewhat flexible yet rigid nature, will snap back and reextend into their original orientation within the groove 40. Preferably, the needle 220 can be inserted into the needle guard 20 in such a way that the user feels or hears a click, which indicates that the needle has been properly engaged and that it should not inadvertently fall out of the needle guard 20.

In the case of medical needles of the wider-winged variety, in which the means for engaging the needle comprises projections 38 engaging holes 126 within the wings 122, no modification of the needle guard 20 is necessary. Regardless of the width of the wings, so long as the holes 126 are situated such that they are in complementary alignment with projections 38, the inventive needle guard 20 can be used to protect needles having a wide variety of differently sized and shaped wing portions 122. Thus, FIG. 4 depicts the same needle guard 20 engaging an alternative medical needle 120 in the same press fit arrangement as the medical needle depicted in FIGS. 2A–2C. Thus, alternative wings 122' include holes 126' similarly situated as holes 126 of the needle 120 depicted in FIGS. 2A–2C such that alternative needle 120' is reliably and securely engaged by the needle guard 20 in the same fashion.

On the other hand, the means for engaging a medical needle 220 having narrower wing portions 227 requires that the interior annular groove 40 be sized so that it can adequately engage the wings 222 in a complementary fashion. Thus, in the case where the needle guard 20 includes a single interior annular groove 40 as depicted in FIGS. 3A–3C, the needle guard 20 will only be able to accommodate a medical needle 220 having winged portions 222 within a relatively narrow range of sizes.

Figure 5B:
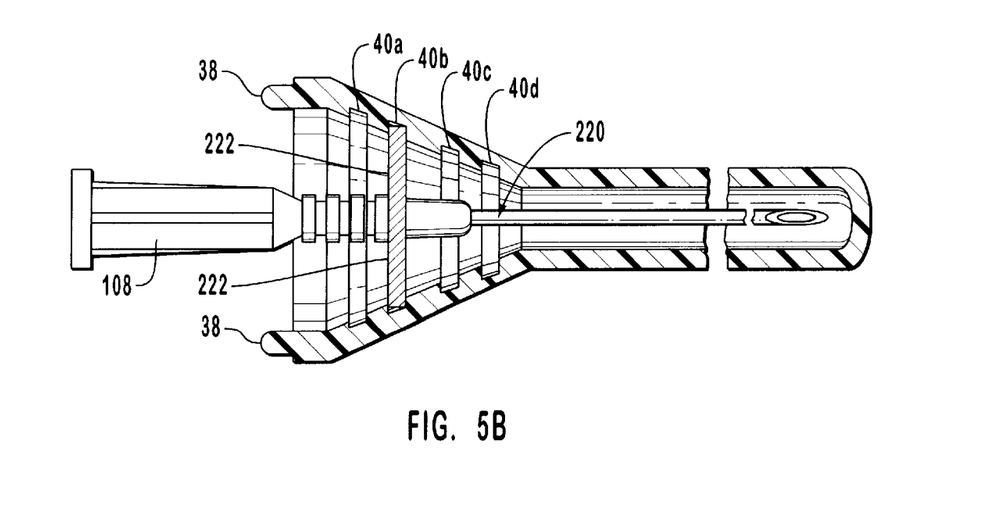
FIG. 5B is a side cross-sectional view of the flared portion of a needle guard in accordance with the present invention cut along line 5B—5B of FIG. 5A.

Therefore, in order to accommodate a wider variety of narrower-winged needles 220 having significantly varying wing sizes, the needle guard 20 can be manufactured to include a plurality of interior annular grooves 40, as depicted in FIGS. 5A and 5B. The inclusion of multiple annular grooves 40 can easily accommodate varying sizes of wing portions 222 since the wings will simply bypass those grooves which are too large but engage the appropriate groove having a corresponding diameter. Conversely, upon engaging with the proper groove, the needle 220 will be prevented from advancing further into the needle guard such that the needle 220 will not engage grooves that have too narrow of a diameter. In other words, proper engagement of the wings with the corresponding groove is self selecting such that the wings will find and engage the properly-sized annular groove 40. Although FIGS. 5A and 5B depict four grooves 40a, 40b, 40c and 40d, needle guards according to the present invention may include any feasible and practical number of interior annular grooves 40.

Depending on the intended use of the needle guard, the distal end 28 of the hollow body 22 can either be open as illustrated in FIGS. 2A–2C, or closed as illustrated in FIGS. 3A–3C. The distal end 28 of the hollow body is preferably closed when it is desired to keep fluid from the needle housed in the needle guard 20 from escaping, or to prevent external fluids from contaminating the needle. Alternatively, it will be preferable for the distal end 28 of the needle guard 20 to be open in the event that fluid communication with the needle is desired, such as for the purpose of cleaning or washing a needle while housed within the needle guard 20.

The flared portion can extend radially and axially from the elongated hollow body at any desired angle that will allow the annular groove 40 to engage the wings 222 of a medical needle 220 having narrower-wing portions and that will allow the projections 38 extending from the lip 24 to engage the wings of a medical needle 120 having longer-wing portions.

The needle guard may be manufactured using any appropriate material that is sufficiently sturdy to prevent the tips of the medical needles inserted therein from penetrating through the flared portion of the needle guard as the needle is inserted into the needle guard, or through the elongated hollow body portion while the medical needle is being stored or disposed of. Appropriate materials include polymers, plastics, glass, metal, and combinations thereof. Plastics and polymers are preferred over glass due to their greater durability, and preferred over metal due to their ease in molding.

The present invention may be embodied in other specific forms without departing from its spirit or essential characteristics. The described embodiments are to be considered in all respects only as illustrated and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A prophylactic needle guard for use in combination with a medical needle having a wing portion extending from the medical needle, the needle guard comprising:
   an elongated hollows body;
   a hollow flared portion extending from an end of the hollow body, the flared portion having a first end comprising a lip defining an opening and a second end connected to the end of the hollow body and wherein the first end of the flared portion has a diameter smaller than the width of the wing portion of the medical needle; and
   means, formed on said hollow flared portion, for engaging a wing portion of a medical needle upon inserting the medical needle into the needle guard in order to selectively retain the medical needle within the needle guard and wherein the means for engaging a wing portion of a medical needle includes at least one projection extending from the lip for engaging a corresponding recess within the wing portion of the medical needle when the medical needle is inserted within the needle guard.

2. A prophylactic needle guard as defined in claim 1, wherein the needle guard comprises a pair of projections extending from the lip configured to engage a pair of corresponding recesses within the wing portion of the medical needle engagement.

3. A prophylactic needle guard as defined in claim 1, wherein the projection is configured to engage the corresponding recess within the wing portion of the medical needle in a press-fit engagement.

4. A prophylactic needle guard as defined in claim 1, wherein the projection is configured to engage the corresponding recess within the wing portion of the medical needle in a snap-fit engagement.

5. A prophylactic needle guard as defined in claim 1, wherein the hollow body further includes an open end distal to where the hollow body is attached to the flared portion.

6. A prophylactic needle guard as defined in claim 1, wherein the hollow body further includes a closed end distal to where the hollow body is attached to the flared portion.

7. A prophylactic needle guard for use in combination with a variety of different medical needles having a winged portion extending from the medical needle and wherein a winged portion of at least one medical needle is different in size from the others, the needle guard comprising:
   an elongated hollow body;
   a hollow flared portion extending from an end of the hollow body, the flared portion having a first end comprising a lip defining an opening and an outer diameter the flared portion also having a second end connected to the end of the hollow body;
   first engaging means formed on said hollow flared portion, for engaging the wing portion of a first medical needle; and
   second engaging means formed on said hollow flared portion, for engaging the wing portion of the at least one medical needle.

8. A prophylactic needle guard as defined in claim 7, wherein the first engagement means includes a pair of projections extending from the lip of the flared portion configured to engage a pair of corresponding openings within the wing portion of the first medical needle.

9. A prophylactic needle guard as defined in claim 8, wherein insertion of the pair of projections extending from the lip of the flared portion into the pair of corresponding openings within the wing portion of the first medical needle provide means for indicating when the first medical needle has been reliably engaged with the needle guard.

10. A prophylactic needle guard as defined in claim 7, wherein the second engagement means includes at least one interior annular groove disposed within an inner surface of the flared portion for engaging the wing portion of the second medical needle.

11. A prophylactic needle guard as defined in claim 10, wherein placement of the second medical needle within the needle guard such that the wing portion of the second medical needle snaps in place within the interior annular groove provides means for indicating when the second medical needle has been securely engaged with the needle guard.

12. A prophylactic needle guard as defined in claim 7, wherein the second engaging means includes a plurality of interior annular grooves having varying diameters in order to selectively engage one of a plurality of medical needles having differently-sized wing portions.

13. A prophylactic needle guard for use in combination with a medical needle having a wing portion, the needle guard comprising:

an elongated hollow body;

a hollow flared portion extending radially from an end of the hollow body, the flared portion having an inner surface and a first end comprising a lip defining an opening and a second end connected to the hollow body;

at least one projection extending from the lip of the hollow flared portion for engaging one or more corresponding openings within a wing portion of a first medical needle upon inserting the first medical needle into the needle guard; and at least one interior annular groove disposed on the inner surface of the flared portion for engaging a corresponding wing portion of a second medical needle upon alternatively inserting the second medical needle into the needle guard.

14. A prophylactic needle guard as defined in claim 13, wherein insertion of the at least one projection extending from the lip of the hollow flared portion into the one or more corresponding openings within the wing portion of the first medical needle provides means for indicating when the first medical needle has been reliably engaged with the needle guard.

15. A prophylactic needle guard as defined in claim 13, wherein the needle guard includes a pair of projections extending from the lip of the hollow flared portion for engaging a corresponding pair of openings within the wing portion of the first medical needle upon inserting the first medical needle into the needle guard.

16. A prophylactic needle guard as defined in claim 13, wherein placement of the second medical needle within the needle guard such that the wing portion of the second medical needle snaps in place within the interior annular groove provides means for indicating that the second medical needle has been securely engaged with the needle guard.

17. A prophylactic needle guard as defined in claim 13, wherein the needle guard includes a plurality of interior annular grooves having varying diameters in order to selectively engage one of a plurality of medical needles having differently-sized wing portions.

18. A prophylactic needle guard for use in combination with a medical needle having a wing portion extending from the medical needle, the needle guard comprising:

an elongated hollow body;

a hollow flared portion extending from an end of the hollow body, the flared portion having a first end comprising a lip defining an opening and a second end connected to the end of the hollow body and wherein the first end of the flared portion has a diameter larger than the width of the wing portion of the medical needle; and means, formed on said hollow flared portion, for engaging a wing portion of a medical needle upon inserting the medical needle into the needle guard in order to selectively retain the medical needle within the needle guard and wherein the means for engaging a wing portion of a medical needle comprises an interior annular groove disposed on an inner surface of the flared portion such that upon inserting the medical needle into the needle guard, the wing portion will enrage the annular ring in a snap-fit engagement.

19. A prophylactic needle guard as defined in claim 18, wherein the needle guard includes a plurality of interior annular grooves having varying diameters in order to selectively engage one of a plurality of medical needles having differently-sized wing portions.

* * * * *

UNITED STATES PATENT AND TRADEMARK OFFICE
CERTIFICATE OF CORRECTION

PATENT NO. : 6,059,758
DATED : May 9, 2000
INVENTOR(S) : William Padilla, Garlyn W. Hendry It is certified that error appears in the above-identified patent and that said Letters Patent is hereby corrected as shown below:

Col. 1, ln. 65: after "extending" change "form" to --from--

Col. 2, ln. 47: after "having" change "a" to --an--

Col. 3, ln. 55: after "extending" change "form" to --from--

Col. 4, ln. 11: after "wings" change "in" to --is--

Col. 4, ln. 54: before "medical" change "narrowerwinged" to --narrower-winged--

Col. 9, ln. 47: after "only as" change "illustrated to --illustrative--

Signed and Sealed this

Tenth Day of April, 2001

Attest:

NICHOLAS P. GODICI

Attesting Officer

Acting Director of the United States Patent and Trademark Office